US005488035A

United States Patent [19]

Rao

[11] Patent Number: 5,488,035
[45] Date of Patent: Jan. 30, 1996

[54] PEPTIDE WITH INHIBITORY ACTIVITY TOWARDS PLANT PATHOGENIC FUNGI

[75] Inventor: Aragula G. Rao, Polk County, Iowa

[73] Assignee: Pioneer Hi-Bred International, Inc., Des Moines, Iowa

[21] Appl. No.: 802,794

[22] Filed: Dec. 6, 1991

[51] Int. Cl.⁶ .......................... A61K 38/00; A61K 38/04; C07K 5/00; C07K 7/00
[52] U.S. Cl. ................. 514/13; 530/326; 47/58; 47/DIG. 1
[58] Field of Search ................. 514/13; 530/326

[56] References Cited

U.S. PATENT DOCUMENTS

| 4,202,892 | 5/1980 | Weiner et al. | 514/212 |
| 4,254,128 | 3/1981 | Weiner et al. | 514/183 |
| 4,618,616 | 10/1986 | Richardson et al. | 514/340 |
| 4,822,822 | 4/1989 | Arita et al. | 514/655 |
| 4,935,520 | 6/1990 | Nojima et al. | 546/22 |
| 4,960,782 | 10/1990 | Gymer et al. | 514/383 |

FOREIGN PATENT DOCUMENTS 0348348  12/1989  European Pat. Off. .

OTHER PUBLICATIONS

Miyata et al. J. Biochem. 106(4) 663–668 (1989).
Kawano et al. J. Biol. Chem. 265(26) 15365–7 (1990).
Nakamura et al. J. Biol. Chem. 263(32) 16709–16713 (1988).
Vigers, Alison J. et al. (1992) Thaumatin–like pathogenesis–related proteins are antifungal, *Plant Science,* vol. 83, pp. 155–161.
Week 9038, Derwent Publications, Ltd., London, G.B.; AN 90–287871 & JP–A–2 204 500 (Taiyo Fishery) 14 Aug. 1990.

*Primary Examiner*—Jill Warden
*Assistant Examiner*—A. M. Davenport
*Attorney, Agent, or Firm*—Pioneer Hi-Bred International, Inc.

[57] ABSTRACT

The peptide tachyplesin has been found to have antimicrobial activity against plant pathogens. In a preferred embodiment, plant resistance to diseases caused by plant pathogens which are susceptible to this peptide proteins is produced by inserting into the cells of a plant a gene whose expression causes production of tachyplesin in the plant in antimicrobial amounts.

5 Claims, No Drawings

PEPTIDE WITH INHIBITORY ACTIVITY TOWARDS PLANT PATHOGENIC FUNGI

TECHNICAL FIELD

This invention relates to materials and methods for killing fungi and other microorganisms which are harmful to plants, and materials and methods for imparting disease resistance to plants.

BACKGROUND OF THE INVENTION

Numerous fungi and bacteria are serious pests of common agricultural crops. One method of controlling diseases has been to apply antimicrobial organic or semiorganic chemicals to crops. This method has numerous, art-recognized problems. A more recent method of control of microorganism pests has been the use of biological control organisms which are typically natural competitors or inhibitors of the troublesome microorganisms. However, it is difficult to apply biological control organisms to large areas, and even more difficult to cause those living organisms to remain in the treated area for an extended period. Still more recently, techniques in recombinant DNA have provided the opportunity to insert into plant cells cloned genes which express antimicrobial compounds. This technology has given rise to additional concerns about eventual microbial resistance to well-known, naturally occurring antimicrobials, particularly in the face of heavy selection pressure, which may occur in some areas. Thus, a continuing need exists to identify naturally occurring antimicrobial compounds which can be formed by plant cells directly by translation of a single structural gene.

European Patent Application 204,590, based upon U.S. patent application Ser. No. 725,368, describes a method of genetically modifying a plant cell to control expression of heterologous foreign structure genes. In the method, the plant cell is transformed to contain a pRi T-DNA promoter and a heterologous foreign structural gene, the promoter and the structural gene being in such position and orientation with respect to one another that the structural gene is expressible in a plant cell under control of the promoter.

Likewise, European Patent Application 186,425, based upon U.S. patent application Ser. No. 685,824, describes a recombinant DNA expression vector which comprises (a) a transcription unit, flanked by T-DNA border sequences, which comprises a promoter and associated amino terminal region encoding sequences and a terminator signal sequence in which the sequences are derived from one or more genes which are naturally expressed in a plant cell, and (b) an antibiotic resistance gene-encoding sequence located between the promoter and associated amino-terminal region-encoding sequence and the terminator sequence and (c) a DNA fragment containing a replicon that is functional in Agrobacterium.

PCT application 8807087, based upon U.S. patent application Ser. No. 168,109, discloses a recombinant virus expression system comprising a Heliothis polyhedrin promoter and a nucleotide sequence encoding a heterologous peptide or protein, which may have antimicrobial activity.

Akaji, K. et al., *Chem. Pharm. Bull. (Tokyo)* 37(10):2661–2664 (1989), reports the syntheses of three peptides from horseshoe crab, including tachyplesin I and II.

Kawano, K. et al., *J. Biol. Chem.* 265(26):15365–15367 (1990), reports the isolation of tachyplesin I from hemocytes of the horseshow crab, and determination of its betasheet structure.

Miyata, T. et al., *J. Biochem. (Tokyo)* 106(4):663–669 (1989), discloses isolation of tachyplesin II from horseshoe crab and elucidation of its structure and biological activity.

Muta, T. et al., *J. Biochem. (Tokyo)* 108(2):261–266 (1990), discloses isolation of tachyplesin III and a processing intermedate of its precursor.

Nakamura, T. et al., *J. Biol. Chem.* 263(32):16709–16713 (1988), discusses isolation and chemical structure of tachyplesin.

Niwa, M. et al., *First Scientific Meeting of the Japanese Association for Developmental and Comparative Immunology (Jadci), Tokyo., Japan, November* (14(2):2–3 (1990) deals with the antimicrobial activities of tachyplesin isopeptides.

Shieh, T. C. et al., *FEBS (Fed. Eur. Biochem. Soc.) Lett.* 252(1–2):121–124 (1989) discloses synthesis and properties of tachyplesin I.

Shigenaga, T. et al., *J. Biol. Chem.* 265(34):21350–21354 (1990) describes cloning of cDNA for the peptide precursor of tachyplesin and the cellular localization of the peptide in the horseshoe crab.

Japanese laid-open patent application 02207098, assigned to Taiyo Fishery KK, disloses a composition having high specificity to beta-glucan. The composition includes an amoebocyte lysate from Lumulina and blood cell membrane proteins including tachyplesins I and II.

Japanese laid-open patent application 02204500, also assigned to Taiyo Fishery KK, discloses an article insoluble carrier for removing pyrogens from fluids. The article is made by bonding crab peptides identified as tachyplesins I and II to a water insoluble carrier.

The disclosures of the foregoing references are hereby incorporated herein in their entirety by reference to show the state of the art.

DISCLOSURE OF THE INVENTION

It has now been determined that the peptide tachyplesin has potent antimicrobial activity against common plant pathogens. Tachyplesin is a small peptide originally isolated from the hemocytes of the horseshoe crab, *Tachypleus tridentatus*. The peptide has 17 amino acids, six of which are cysteines. Japanese investigators have reported the peptide to be active against Gram positive and Gram negative bacteria, as well as *Candida albicans*. Tachyplesin's conformation consists of an antiparallel β-sheet connected by a β-turn. Five bulky hydrophobic side groups are localized on one side of the plane and six cationic side groups are distributed at the tail part of the molecule. There are three known isopeptides, designated as tachyplesin I, II and III. The peptide can also exist either in straight chain form, referred to in the Examples as the "crude" form, or in the form in which disufide bridges have formed between opposing cysteine residues in the molecule, referred to in the Examples as the "oxidized" form. The compound reported in the prior art has an amidated arginine residue at the carboxyl terminus, while the compound employed in the Examples was synthesized with a carboxyl group on the carboxy-terminal arginine residue. For the purposes of this invention any or all of the forgoing peptide forms can be used interchangeably or in combination, and for simplicity will be referred to herein as a single peptide, "tachyplesin," herein. This peptide is particularly active against the following group of plant pathogenic fungi and seed pathogens, *Fusarium graminearum, Fusarium moniliforme, Sclerotinia*

*sclerotiorum, Sclerotinia trifoliorum,* and *Aspergillus flavus.* All of these fungi have significant economic impact. This peptide is particularly active against the recalcitrant fungus *Aspergillus flavus,* and thus could have an effect in reducing aflatoxin contamination of stored grain.

Thus, this invention provides a method for killing susceptible plant pathogens, including microorganisms selected from the group listed above comprising the step of introducing into the environment of the organisms an antimicrobial amount of tachyplesin. Tachyplesin can be effectively applied to plants infested with the microorganisms by spray, dust or other formulation common to the antimicrobial arts. Alternatively, the peptide can be incorporated into the tissues of a susceptible plant so that in the course of infesting the plant the pathogens will be exposed to antimicrobial amounts of the peptide. One method of doing this is to incorporate the tachyplesin in a nonphytotoxic vehicle which is adapted for systemic administration to the susceptible plants. This method is commonly employed with insecticidal materials which are designed to attack chewing insects and is well within the purview of one of ordinary skill in the art of insecticide and larvicide formulation. However, since the gene which codes for tachyplesin can be isolated, cloned, inserted into an appropriate expression cassette, and introduced into cells of a susceptible plant species, an especially preferred embodiment of this method involves inserting into the genome of the plant a DNA sequence coding for tachyplesin in proper reading frame, together with transcription initiator and promoter sequences active in the plant. Transcription and translation of the DNA sequence under control of the regulatory sequences causes expression of the tachyplesin sequence at levels which provide an antimicrobial amount of the peptide in the tissues of the plant which are normally infected by the pathogens. With a working knowledge of conventional techniques for cloning, DNA isolation, amplification and purification, for enzymatic reactions involving DNA ligase, DNA polymerase, restriction endonucleases and the like, and various separation techniques known and commonly employed by those skilled in the art (See, for example, R. Wu, ed. (1979) *Meth. Enzymol.* 68; R. Wu et al., eds. (1983) *Meth. Enzymol.* 100, 101: L. Grossman and K. Moldave, eds. (1980) *Meth. Enzymol.* 65: J. H. Miller (1972) Experiments in Molecular Genetics; R. Davis et al. (1980) *Advanced Bacterial Genetics;* R. F. Schleif and P. C. Wensink (1982) *Practical Methods in Molecular Biology;* and T. Manniatis et al. (1982) *Molecular Cloning.*), one of ordinary skill can employ any suitable gene construct containing the tachyplesin structural gene in the practice of this invention.

The plant is preferably a plant susceptible to infection and damage by one or more of *Fusarium graminearum, Fusarium moniliforme, Sclerotinia sclerotiorum, Sclerotinia trifoliorum, Aspergillus flavus.* These include corn (*Zea mays*) and sorghum (*Sorghum bicolor*). However, this is not to be construed as limiting, inasmuch as these species are among the most difficult commercial crops to reliably transform and regenerate, and these microorganisms also infect many other crops. Thus the methods of this invention are readily applicable via conventional techniques to numerous plant species, if they are found to be susceptible to the plant pests listed hereinabove, including, without limitation, specie s from the genera Fragaria, Lotus, Medicago, Onobrychis, Trifolium, Trigonella, Vigna, Citrus, Linum, Geranium, Manicot, Daucus, Arabidopsis, Brassica, Raphanus, Sinapis, Atropa, Capsicum, Datura, Hyoscyamus, Lycopersionn, Nicotiana, Solanum, Petunia, Digitalis, Majorana, Cichorium, Helianthus, Lactuca, Bromus, Asparagus, Antirrhinum, Hemerocallis, Nemesia, Pelargonium, Panicum, Pennisetum, Ranunculus, Senecio, Salpiglossis, Cucumis, Browallia, Glycine, Lolium, Triticum, and Datura.

Preferred plants that are to be transformed according to the methods of this invention are cereal crops, including maize, rye, barley, wheat, sorghum, oats, millet, rice, triticale, sunflower, alfalfa, rapeseed and soybean.

The DNA sequence which when expressed imparts antimicrobial activity is a structural gene which codes for tachyplesin.

The DNA sequence which codes for tachyplesin can be obtained by conventional techniques and the gene can then be removed by use of appropriate restriction enzymes and spliced into a selected plant expression cassette. Alternatively, purified tachyplesin can be sequenced in its entirety using known methods, and any of several translationally equivalent synthetic DNA sequences can then be prepared which code for the sequence of amino acids, and this synthetic sequence can be inserted into an appropriate plant expression cassette.

Likewise, numerous plant expression cassettes and vectors are well known in the art. By the term "expression cassette" is meant a complete set of control sequences including initiation, promoter and termination sequences which function in a plant cell when they flank a structural gene in the proper reading frame. Expression cassettes frequently and preferably contain an assortment of restriction sites suitable for cleavage and insertion of any desired structural gene. It is important that the cloned gene have a start codon in the correct reading frame for the structural sequence. In addition, the plant expression cassette preferably includes a strong constitutive promoter sequence at one end to cause the gene to be transcribed at a high frequency, and a poly-A recognition sequence at the other end for proper processing and transport of the messenger RNA. An example of such a preferred (empty) expression cassette into which the cDNA of the present invention can be inserted is the pPHI414 plasmid developed by Beach et al. of Pioneer Hi-Bred International, Inc., Johnston, IA, as described in U.S. patent application Ser. No. 387,739, filed Aug. 1, 1989, and its continuation-in-part, Ser. No. 785,648, filed Oct. 31, 1991, the disclosures of which are hereby incorporated herein by reference in their entirety. Highly preferred plant expression cassettes will be designed to include one or more selectable marker genes, such as kanamycin resistance or herbicide tolerance genes.

By the term "vector" herein is meant a DNA sequence which is able to replicate and express a foreign gene in a host cell. Typically, the vector has one or more endonuclease recognition sites which may be cut in a predictable fashion by use of the appropriate enzyme. Such vectors are preferably constructed to include additional structural gene sequences imparting antibiotic or herbicide resistance, which then serve as markers to identify and separate transformed cells. Preferred markers/selection agents include kanamycin, chlorosulfuron, phosphonothricin, hygromycin and methotrexate. A cell in which the foreign genetic material in a vector is functionally expressed has been "transformed" by the vector and is referred to as a "transformant."

A particularly preferred vector is a plasmid, by which is meant a circular double-stranded DNA molecule which is not a part of the chromosomes of the cell.

As mentioned above, either genomic or cDNA which codes for tachyplesin may be used in this invention. The vector of interest may also be constructed partially from a cDNA clone and partially from a genomic clone. When the gene has been isolated, genetic constructs are made which contain the necessary regulatory sequences to provide for efficient expression of the gene in the host cell. According to this invention, the genetic construct will contain (a) a first genetic sequence coding for tachyplesin and (b) one or more regulatory sequences operably linked on either side of the structural gene of interest. Typically, the regulatory sequences will be selected from the group comprising promoters and terminators. The regulatory sequences may be from autologous or heterologous sources.

Promoters that may be used in the genetic sequence include nos, ocs, phaseolin and CaMV promoters.

An efficient plant promoter that may be used is an overproducing plant promoter. Overproducing plant promoters that may be used in this invention include the promoter of the small sub-unit (ss) of the ribulose-1,5-biphosphate carboxylase from soybean (Berry-Lowe et al, *J. Molecular and App. Gen.*, 1:483–498 (1982)), and the promoter of the cholorophyll a-b binding protein. These two promoters are known to be light-induced, in eukaryotic plant cells (see, for example, *Genetic Engineering of Plants, An Agricultural Perspective*, A. Cashmore, Pelham, N.Y., 1983, pp. 29–38, G. Coruzzi et al., *J. Biol. Chem.*, 258:1399 (1983), and P. Dunsmuir, et al., *J. Molecular and App. Gen.*, 2:285 (1983)).

The expression cassette comprising the structural gene for tachyplesin operably linked to the desired control sequences can be ligated into a suitable cloning vector. In general, plasmid or vital (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the tachyplesin gene can be isolated in significant quantities for introduction into the desired plant cells. Host cells that can be used in the practice of this invention include prokaryotes, including bacterial hosts such as *E. coli, S. typhimurium*, and *Serratia marcescens*. Eukaryotic hosts such as yeast or filamentous fungi may also be used in this invention. Since these hosts are also microorganisms, it will be essential to ensure that plant promoters which do not cause expression of the tachyplesin in bacteria are used in the vector, or that a host microorganism which is resistant to tachyplesin is used.

The isolated cloning vector will then be introduced into the plant cell using any convenient technique, including electroporation (in protoplasts), retroviruses, bombardment, and microinjection, into cells from monocotyledonous or dicotyledonous plants, in cell or tissue culture, to provide transformed plant cells containing as foreign DNA at least one copy and preferably more than one copy of the DNA sequence of the plant expression cassette. Preferably, the monocotyledonous species will be selected from maize, sorghum, wheat and rice, and the dicotyledonous species will be selected from soybean, alfalfa, tobacco and tomato. Using known techniques, protoplasts can be regenerated and cell or tissue culture can be regenerated to form whole fertile plants which carry and express the gene for tachyplesin. Accordingly, a highly preferred embodiment of the present invention is a transformed maize plant, the cells of which contain as foreign DNA at least one copy of the DNA sequence of an expression cassette of this invention.

Finally, this invention provides methods of imparting resistance to diseases caused by microorganisms selected from *Fusarium graminearum, Fusarium moniliforme, Sclerotinia sclerotiorum, Sclerotinia trifoliorum, Aspergillus flavus* to plants of a susceptible taxon, comprising the steps of:

a) culturing regenerable cells or tissues from at least one plant from the taxon, b) introducing into the cells of the cell or tissue culture at least one copy of an expression cassette comprising a gene which codes for tachyplesin, operably linked to plant regulatory sequences which cause the expression of tachyplesin in the cells, and c) regenerating disease-resistant whole plants from the cell or tissue culture. Once whole plants have been obtained, they can be sexually or clonally reproduced in such manner that at least one copy of the sequence provided by the expression cassette is present in the cells of progeny of the reproduction.

Alternatively, once a single transformed plant has been obtained by the foregoing recombinant DNA method, conventional plant breeding methods can be used to transfer the structural gene for tachyplesin and associated regulatory sequences via crossing and backcrossing. Such intermediate methods will comprise the further steps of a) sexually crossing the disease-resistant plant with a plant from the disease-susceptible taxon;

b) recovering reproductive material from the progeny of the cross; and c) growing disease-resistant plants from the reproductive material. Where desirable or necessary, the agronomic characteristics of the susceptible taxon can be substantially preserved by expanding this method to include the further steps of repetitively:

a) backcrossing the disease-resistant progeny with disease-susceptible plants from the susceptible taxon; and b) selecting for expression of antimicrobial activity (or an associated marker gene) among the progeny of the backcross, until the desired percentage of the characteristics of the susceptible taxon are present in the progeny along with the gene imparting antimicrobial activity.

By the term "taxon" herein is meant a unit of botanical classification of genus or lower. It thus includes genus, species, cultivars, varieties, variants, and other minor taxonomic groups which lack a consistent nomenclature.

It will also be appreciated by those of ordinary skill that the plant vectors provided herein can be incorporated into *Agrobacterium tumefaciens*, which can then be used to transfer the vector into susceptible plant cells, especially those from dicotyledonous species. Thus, this invention provides a method for imparting antimicrobial activity and disease resistance in *Agrobacterium tumefaciens*-susceptible dicotyledonous plants in which the expression cassette is introduced into the cells by infecting the cells with *Agrobacterium tumefaciens*, a plasmid of which has been modified to include a plant expression cassette of this invention.

The following description further exemplifies the compositions of this invention and the methods of making and using them. However, it will be understood that other methods, known by those of ordinary skill in the art to be equivalent, can also be employed.

INDUSTRIAL APPLICABILITY

Example 1

Tachyplesin for this and the other Examples was synthesized from the known amino acid sequence and structure, according to methods reported in the literature, specifically the "Fastmoc" method described by C. G. Fields, et al., *Peptide Res.*, Vol. 4 pp.95–101 (1991). Since the peptide and its synthesis are both known, neither one per se is considered a part of this invention. The peptide was synthesized with a carboxyl group on the carboxy-terminal arginine residue rather than the amidated arginine reported in the articles from the Japanese researchers cited above.

The tachyplesin was used at a concentration of 100 μg/ml as determined by absorption spectrum was screened against four common plant pathogens in both crude and oxidized forms. Antifungal activity was scored on a scale of 0 to 4, with 0 being no inhibition observed relative to a water control, and 4 being complete inhibition. Two reps were done for each treatment. Results were as follows:

| Fungus | Prep | Score |
|---|---|---|
| *Fusarium graminearum*, isolate 8 | crude | 4.0 |
|  | oxidized | 4.0 |
| *Fusarium graminearum*, isolate 5 | crude | 4.0 |
|  | oxidized | 4.0 |
| *Aspergillus flavus*, isolate 1 | crude | 3.5 |
|  | oxidized | 3.5 |
| *Sclerotinia trifoliorum*, isolate 1 | crude | 4.0 |
|  | oxidized | 4.0 |

Example 2

Decreasing tested concentrations of tachyplesin were against the preceding four organisms plus *Fusarium moniliforme* and *Sclerotinia sclerotiorum* to determine the minimum inhibitory concentration, and this was compared with other antimicrobial compounds. Results were as follows:

their suitability as plant antimicrobials under varying conditions. None of the antimicrobials showed a discernible trend or optimum across a range of buffer pHs of from 5.0 to 8.0. However, the MICs of defensin and hordothionin against *A. flavus* were higher and increased dramatically (4× to 8×) over NaCl concentrations of from 0 to 100 mM, while the MIC of tachyplesin was lower and nearly constant (<20 μg/ml) over NaCl concentrations of from 0 to 125 mM against *A. flavus*.

What is claimed is:

1. A method for killing and inhibiting plant pathogenic fungi which are susceptible to tachyplesin, comprising introducing into the environment of the pathogenic microorganisms an antimicrobial amount of tachyplesin.

2. A method for killing and inhibiting plant pathogenic fungi selected from *Fusarium graminearum, Fusarium moniliforme, Sclerotinia sclerotiorum, Sclerotinia trifoliorum,* and *Aspergillus flavus,* comprising introducing into the environment of the pathogenic fungi an antimicrobial amount of tachyplesin.

3. A method according to claim 2 wherein the environment of the pathogenic fungi is the tissues of a living plant.

4. An antifungal composition for application to plants, comprising an antifungal amount of tachyplesin in a nonphytotoxic vehicle.

| μg/ml | μM | prep | FGR 005 | FGR 008 | FMO 001 | AFL 001 | SSC 002 | SSC ascospores |
|---|---|---|---|---|---|---|---|---|
| 100 | 44.4 | crude | 4.0 | 4.0 | 4.0 | 3.5 | 4.0 | 4.0 |
|  |  | oxidized | 4.0 | 4.0 | 4.0 | 3.75 | 4.0 | 4.0 |
| 50 | 22.2 | crude | 4.0 | 4.0 | 4.0 | 3.25 | 4.0 | 4.0 |
|  |  | oxidized | 4.0 | 4.0 | 4.0 | 3.75 | 4.0 | 4.0 |
| 25 | 11.1 | crude | 4.0 | 4.0 | 3.75 | 1.5 | 4.0 | 4.0 |
|  |  | oxidized | 4.0 | 4.0 | 4.0 | 2.75 | 4.0 | 4.0 |
| 12.5 | 5.6 | crude | 3.0 | 3.75 | 1.25 | 1.0 | 1.0 | 4.0 |
|  |  | oxidized | 3.5 | 4.0 | 2.5 | 1.5 | 4.0 | 4.0 |
| 6.25 | 2.8 | crude | 1.0 | 0.0 | 0.5 | 0.0 | 0.0 | 0.0 |
|  |  | oxidized | 2.25 | 2.0 | 1.0 | 1.0 | 0.0 | 3.0 |
| 3.13 | 1.4 | crude | 0.0 | 0.0 | 0.0 | 0.0 | 0.0 | 0.0 |
|  |  | oxidized | 0.0 | 0.0 | 0.5 | 0.0 | 0.0 | 0.0 |
| 1.56 | 0.7 | crude | 0.0 | 0.0 | 0.0 | 0.0 | 0.0 | 0.0 |
|  |  | oxidized | 0.0 | 0.0 | 0.0 | 0.0 | 0.0 | 0.0 |

| MIC Comparisons: | MIC μg/ml (μM) | | | |
|---|---|---|---|---|
| Protein | AFL 001 | FGR 005 | FMO 001 | SSC 002 |
| tachyplesin, | 6.25 (2.8) | 6.25 (2.8) | 6.25 (2.8) | 12.5 (5.6) |
| defensin | 11.7 (3) | 2.6 (0.7) | 11.7 (3) | 12.5 (3.2) |
| hordothionin | 15 (3) | 5 (1) | 45 (9) | 30 (6) |
| CMIII | 60 (15) | 6.2 (1.6) | 18.2 (4.6) | 24 (6) |

Example 3

The MICs of tachyplesin, defensin and hordothionin (μg/ml) were measured against FGR 008 and AFL 001 across a range of buffer pHs and ionic strengths to determine 5. A composition according to claim 4 wherein the vehicle is adapted for systemic administration to a plant that is susceptible to plant pathogenic fungi.

* * * * *